United States Patent
Seeley et al.

(10) Patent No.: US 7,378,385 B2
(45) Date of Patent: May 27, 2008

(54) ROLE FOR GLP-1 TO MEDIATE RESPONSES TO DISPARATE STRESSORS

(75) Inventors: Randy John Seeley, Hamilton, OH (US); David A. D'Alessio, Cincinnati, OH (US); Kimberley P. Kinzig, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 135 days.

(21) Appl. No.: 10/635,230

(22) Filed: Aug. 6, 2003

(65) Prior Publication Data

US 2004/0116331 A1 Jun. 17, 2004

Related U.S. Application Data

(60) Provisional application No. 60/402,116, filed on Aug. 8, 2002.

(51) Int. Cl.
*A01N 37/00* (2006.01)
(52) U.S. Cl. .......................................... 514/2; 530/300
(58) Field of Classification Search ..................... None
See application file for complete search history.

(56) References Cited

U.S. PATENT DOCUMENTS 5,846,937 A 12/1998 Drucker
6,395,767 B2 5/2002 Robl et al.

OTHER PUBLICATIONS van Dijk et al. Nature, 1997; 385:214.*
Griebel et al. PNAS 2002; 99: 6370-6375.*
Argyropoulos et al. (Pharmacology & Therapeutics, 2000; 88: 213-227.*
Bruce S. McEwen, Brain Res. 2000; 886: 172-189.*
Goke et al., Distribution of GLP-1 Binding Sites in the Rat Brain: Evidence that . . . , Eur. J. Neurosci, 1995, 7:2294-300.
Kinzig et al., CNS Glucagon-Like Peptide-1 Receptors Mediate Endocrine and Anxiety . . . , Journal of Neuroscience, Jul. 16, 2003, 23(15):6163-6170.
Thiele, et al., Research report on Central infusion of glucagon-like peptide-1-(7-36) amid (GLP-1) receptor antagonist attenuates lithium chloride-induced c-Fos induction in rat brainstem, Brain Research 801, 1998, pp. 164-170, Elsiever Science B.V.
Montrose-Rafizadeh, et al., High Potency Antagonists of the Pancreatic Glucagon-like Peptide-1 Receptor, The Journal of Biological Chemistry, vol. 272, No. 34, Aug. 22, 1997, pp. 21201-21206, U.S.A.

* cited by examiner

*Primary Examiner*—Eileen O'Hara
*Assistant Examiner*—Christina Borgeest
(74) *Attorney, Agent, or Firm*—Taft Stettinius & Hollister LLP

(57) ABSTRACT

GLP-1 and GLP-1 receptor antagonists have been found to have a sedative or anxiolytic effect on the mammalian central nervous system. Conversely, GLP-1 and GLP-1 receptor agonists increase nervous system activity and the stress response. The invention relates, in one aspect, to the use of GLP-1 agonists and antagonists to modulate the stress response in a mammal. In an aspect GLP-1 and GLP-1 receptor antagonists are used to treat stress-related disorders.

21 Claims, 5 Drawing Sheets

ROLE FOR GLP-1 TO MEDIATE RESPONSES TO DISPARATE STRESSORS

CROSS-REFERENCE TO RELATED APPLICATIONS

This application claims priority to and benefit of U.S. Provisional Patent Application No. 60/402,116, filed on Aug. 8, 2002, which is herein incorporated by reference in its entirety.

GOVERNMENT GRANT INFORMATION

This invention was made with Government support under Grant No. NIH NIDDK-5-RO1-DK54890. The United States Government has certain rights in this invention.

FIELD OF THE INVENTION

The present invention relates to methods of altering the activity of the mammalian central nervous system. Specifically, the invention relates to the use of GLP-1, and agonists and antagonists thereof, as effectors of the central nervous system.

BACKGROUND

Stress is necessary for animals including humans to adapt their behaviors and physiology to changes in both the internal and external environment. However, such stress responses that are adaptive in the short-term often come at the price of long-term mental and physical health in the form of affective disorders such as depression and posttraumatic stress disorder, systemic diseases such as colitis, hypertension, and asthma, as well as neurodegenerative disease such as Alzheimer's disease (Kathol et al (1989) *Biol. Psychiatry* 25:873-878; Charney et al (1993) *Arch Gen Psychiatry* 50:295-305; McEwen and Stellar (1993) *Arch Intern Med* 153:2093-2101; Landfield and Eldridge (1991) *Acta Endocrinol.* 125:54-64, herein incorporated by reference in their entirety). The development or perpetration of these diseases, among others, may be associated with prolonged exposure to a response that is initially beneficial to the animal's survival (Herman and Cullinan (1997) *Trends Neurosci.* 20:78-84, herein incorporated by reference). Two important aspects of the stress response are increased activity of the hypothalamic-pituitary-adrenal axis (HPA) resulting in increased levels of circulating glucocorticoids, including ACTH and CORT, and a variety of anxiety-related behaviors. Considerable research effort has been expended to understand the neural circuits that mediate both activation of the HPA axis and anxiety-related behaviors in the hopes of finding ways to reduce inappropriate stress that contributes to disease.

Stressors differ greatly in their form and thus may be mediated by distinct neural pathways. Stressors that threaten an organism from the outside such as predators and dangerous locations are termed exteroceptive and often rely on somatosensory and/or nociceptive pathways as their origin. Stressors that threaten an organism from within the internal milieu such as inflammation, hypoxia or toxins are termed interceptive and rely largely upon input from brainstem pathways, which integrate systemic information conveyed via the vagal and glossopharyngeal nerves, as well as signals transduced across the blood-brain-barrier (Li et al (2000)).

GLP-1 is a post-translational product of preproglucagon and is made in L-cells in the distal intestine and thought to have important actions in the peripheral control of glucose homeostasis. Like many gut peptides, GLP-1 is also made in the CNS where it is produced in a discrete population of neurons in the nucleus of the solitary tract (NTS) of the brainstem (Jin et al. (1988) *J. Comp. Neurol.* 271:519-532; Han et al. (1986) *J. Neurosci.* 16:97-107, herein incorporated by reference in their entirety). Signaling by GLP-1 is transduced through a single G-protein-linked receptor (GLP-1R) predominantly expressed in pancreatic islets, lung, stomach, and brain (Thorens et al (1992) *PNAS: USA* 89:8641-8645, herein incorporated by reference in its entirety). In the CNS, GLP-1 has been proposed to be a regulator of food intake since GLP-1 agonists potently inhibit food intake when delivered into the CNS. GLP-1 agonists are currently in clinical development primarily for the treatment of diabetes via GLP-1's peripheral action to increase glucose-dependent insulin secretion and the suppression of hepatic glucose output.

Cholecystokinin (CCK) is a gastrointestinal peptide secreted peripherally after meals and appears to participate in the termination of meals. Additionally, cholecystokinin has had its actions in the CNS linked to the stress response. Parallels exist between GLP-1 and CCK in both peripheral and central action. A number of central nervous system CNS peptide systems have been importantly implicated in stress responses, with corticotropin releasing hormone (CRH) and a number of closely related peptides garnering the most research attention. GLP-1 producing neurons project to a number of brain areas including areas implicated as critical to stress responses such as the central nucleus of the amygdala (CeA) and the paraventricular nucleus of the hypothalamus (PVN) (Goke et al. (1995) *Eur. J. Neurosci* 7:2294-2300), where high concentrations of the GLP-1 receptor are found (Han et al. (1986) *J. Neurosci.* 16:97107; Merchenthaler et al. (1999) *J. Comp Neurol* 403:261-280, herein incorporated by reference in their entirety). Considerable controversy has surrounded the function of GLP-1 in the CNS, but its anatomy is ideally situated to provide interceptive information from the caudal brainstem to the limbic structures implicated in mediating the responses to stress. In addition to an ideal anatomical location, GLP-1 neurons are activated in response to interceptive stressors, such as LiCl, and central GLP-1 activates PVN CRH neurons (Rinaman (1999a) *Am J. Physiol.* 277:R582-R590; Tang-Christensen et al (1996) *Am. J. Physiol.* 271:R848-R856, herein incorporated by reference in their entirety).

SUMMARY OF THE INVENTION

GLP-1 signaling in the CNS is a critical regulator of both the HPA axis (and resulting levels of ACTH and glucocorticoids) and anxiety-related behaviors in rats. Among the observations pertinent to the invention are: (1) GLP-1 agonists administered into the brain of rats result in increased circulating levels of ACTH and glucocorticoids at doses that do not elicit such responses when administered into the periphery; (2) the effect of GLP-1 agonists to increase ACTH and glucocorticoids can be blocked by administration of CRH receptor antagonists suggesting a direct action of GLP-1 to increase activity of the HPA axis; (3) GLP-1R antagonists can block the increased ACTH and glucocorticoid levels induced by interceptive or exteroceptive stress; (4) GLP-1 antagonists lower anxiety-related behavior; and, (5) GLP-1 agonists increase anxiety-related behavior.

Modulations of GLP-1 signaling or downstream elements of GLP-1 signaling could be used to modulate stress responses and activity of the HPA axis. In a preferred embodiment, the invention lowers stress responses and activity of the HPA axis. Manipulations that alter GLP-1 signaling in the CNS or in specific regions of the CNS could be used therefore to treat a wide range of disorders that include heightened stress responses as part of their etiology or symptomaology such as affective disorders, drug and alcohol abuse, anorexia nervosa, bulimia, Cushing's syndrome, immune dysfunction and metabolic diseases characterized by abnormal glucocorticoid levels.

It is a first aspect of the invention to provide a method of sedating a mammalian subject, the method comprising the step of administering an antagonist of GLP-1 or an antagonist of the GLP-1 receptor (GLP-1R) to the mammalian subject in an amount sufficient to produce a sedative or anxiolytic effect on the mammalian subject.

It is a second aspect of the invention to provide a method of sedating a human being, the method comprising the step of administering an antagonist of GLP-1 or an antagonist of the GLP-1 receptor to the human being in an amount sufficient to produce a sedative or anxiolytic effect on the human being.

It is a third aspect of the invention to provide a method of sedating a mammalian subject, the method comprising the step of administering an antagonist of GLP-1 or an antagonist of the GLP-1 receptor to the mammalian subject intracerebroventricularly.

It is a fourth aspect of the invention to provide a method of sedating a human being, the method comprising the step of administering an antagonist of GLP-1 or an antagonist of the GLP-1 receptor to the human being intracerebroventricularly.

It is a fifth aspect of the invention to provide a method of sedating a mammalian subject, the method comprising the step of administering an antagonist of GLP-1 or an antagonist of the GLP-1 receptor to the mammalian subject orally, subcutaneously, intramuscularly, or intravenously.

It is a sixth aspect of the invention to provide a method of sedating a human being, the method comprising the step of administering an antagonist of GLP-1 or an antagonist of the GLP-1 receptor to the human being orally, subcutaneously, intramuscularly, or intravenously.

It is a seventh aspect of the invention to provide a method of sedating a mammalian subject, the method comprising the step of administering an antagonist of GLP-1 or an antagonist of the GLP-1 receptor to the mammalian subject in an amount sufficient to produce a sedative or anxiolytic effect on the mammalian subject, wherein the mammalian subject exhibits a stress-related disorder. Stress-related disorders include, but are not limited to, anxiety, aggression, psychosis, seizures, panic attacks, hysteria, and sleep disorders.

It is an eighth aspect of the invention to provide a method of sedating a human being, the method comprising the step of administering an antagonist of GLP-1 or an antagonist of the GLP-1 receptor to the human being in an amount sufficient to produce a sedative or anxiolytic effect on the human being, wherein the human being exhibits a stress-related disorder. Stress-related disorders include, but are not limited to, anxiety, aggression, psychosis, seizures, panic attacks, hysteria, and sleep disorders.

It is a ninth aspect of the invention to provide a method of altering the circulating levels of adrenocorticotropin (ACTH) and glucocorticoids in a mammalian subject, the method comprising the step of administering GLP-1 antagonists to the brain of the mammalian subject. In an embodiment the circulating level of ACTH increases. In another embodiment, the circulating level of a glucocorticoid increases. Glucocorticoids include, but are not limited to, corticosterone.

It is a tenth aspect of the invention to provide a method of altering the effect of a GLP-1 agonist in a mammalian subject, the method comprising the step of administering a CRH receptor antagonist to the mammalian subject. In an embodiment the effect of a GLP-1 agonist decreases.

It is an eleventh aspect of the invention to provide a method to modulate the effects of an elevated level of a stress-activated hormone within a mammalian subject the method comprising the step of administering GLP-1R antagonists to the mammalian subject. Preferred stress-activated hormones include adrenocorticotropin and glucocorticoids. An elevated level of a stress-activated hormone may result from internal stress or external stress.

It is a twelfth aspect of the invention to provide a method to decrease anxiety related behavior in a mammalian subject, the method comprising the step of administering GLP-1 antagonists to the mammalian subject.

It is a thirteenth aspect of the invention to provide a method to increase anxiety in a mammalian subject, the method comprising the step of administering GLP-1 agonists to the mammalian subject.

It is a fourteenth aspect of the invention to provide a method to modulate the stress response in a mammalian subject, the method comprising the step of administering a GLP-1 agonist to the subject. In an embodiment the GLP-1 agonist is administered to the brain of the subject. In an embodiment the stress response increases. The stress response comprises an endocrine response, an anxiety response, or both an endocrine response and an anxiety response.

It is a fifteenth aspect of the invention to provide a method to preferentially modulate the endocrine response to stress, the method comprising the step of administering a GLP-1 agonist to the paraventricular nucleus of the hypothalamus. In an embodiment, the endocrine response increases.

It is a sixteenth aspect of the invention to provide a method to preferentially modulate the anxiety response to stress, the method comprising the step of administering a GLP-1 agonist to the central nucleus of the amygdala. In an embodiment, the endocrine response increases.

It is a seventeenth aspect of the invention to provide a method to modulate the stress response in a mammalian subject, the method comprising the step of administering a GLP-1 antagonist to the subject. In an embodiment, the GLP-1 antagonist is administered to the subject's brain. In an embodiment, the stress response decreases. In an embodiment the stress response comprises an endocrine response, an anxiety response, or both an endocrine response and an anxiety response.

It is an eighteenth aspect of the invention to provide a method to treat a stress-related disorder, the method comprising the step of administering a therapeutically effective amount of a GLP-1 antagonist to a mammalian subject exhibiting a stress-related disorder. The GLP-1 antagonist may be administered through a variety of methods such as, but not limited to, intracerebroventricularly, orally, subcutaneously, intramuscularly, or intravenously.

Panel A of FIG. 1 presents plasma adrenocorticotropin (ACTH) levels following intracerebroventricular (ICV) administration of multiple GLP-1 levels. The plasma ACTH levels are in pg/ml. Results obtained from saline administration are indicated with squares. Results obtained from administration of 0.1 μg, 1.0 μg, and 10.0 μg GLP-1 are indicated with triangles, inverted triangles, and diamonds respectively.

Panel B of FIG. 1 presents plasma corticosterone (CORT) levels following intracerebroventricular (ICV) administration of multiple GLP-1 levels. Plasma CORT levels are measured in ng/ml. Results obtained from saline administration are indicated with squares. Results obtained from administration of 0.1 μg, 1.0 μg, and 10.0 μg GLP-1 are indicated with triangles, inverted triangles, and diamonds respectively.

Panel C of FIG. 1 presents plasma corticosterone (CORT) levels following intraperitoneal (IP) administration of multiple GLP-1 levels. Plasma CORT levels are measured in ng/ml. Results obtained from saline administration are indicated with squares. Results obtained from administration of 10 μg GLP-1/kg rat, 100 μg GLP-1/kg rat, and 500 μg GLP-1/kg rat are indicated with triangles, inverted triangles, and diamonds respectively.

Panel D of FIG. 1 presents plasma CORT levels following serial administration of saline and saline, astressin and saline, saline and GLP-1, or astressin and GLP-1. The first solution in each treatment was administered by intraperitoneal injection; the second solution was administered by intracerebroventricular injection. Plasma CORT levels are measured in ng/ml. Results obtained from saline administration are indicated with squares. Results obtained from administration of astressin, GLP-1, and both astressin and GLP-1 are indicated with triangles, inverted triangles, and diamonds respectively.

Figure 1A:
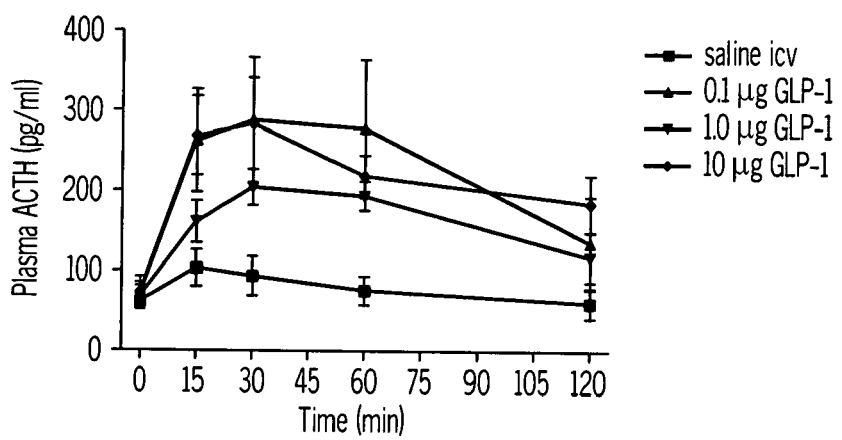
FIG. 1 presents plasma endocrine levels at multiple time points following GLP-1 administration. Plasma endocrine levels at the time of treatment and at 15 minutes, 30 minutes, 60 minutes, and 120 minutes post-treatment are indicated in each graph.
Figure 1B:
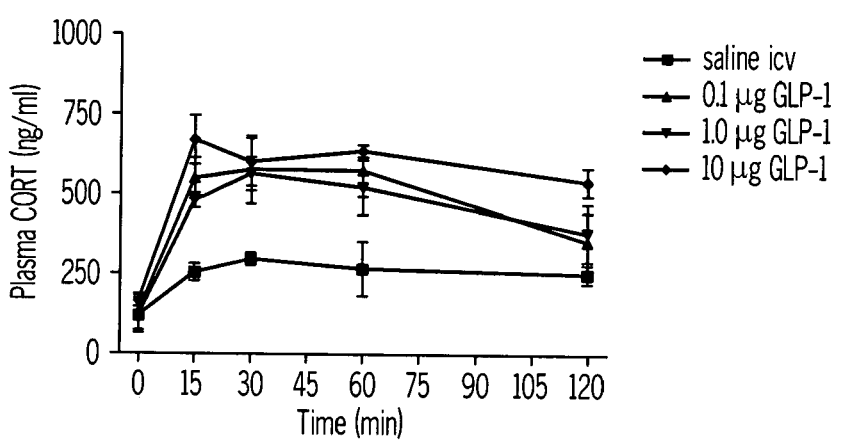
Figure 1C:
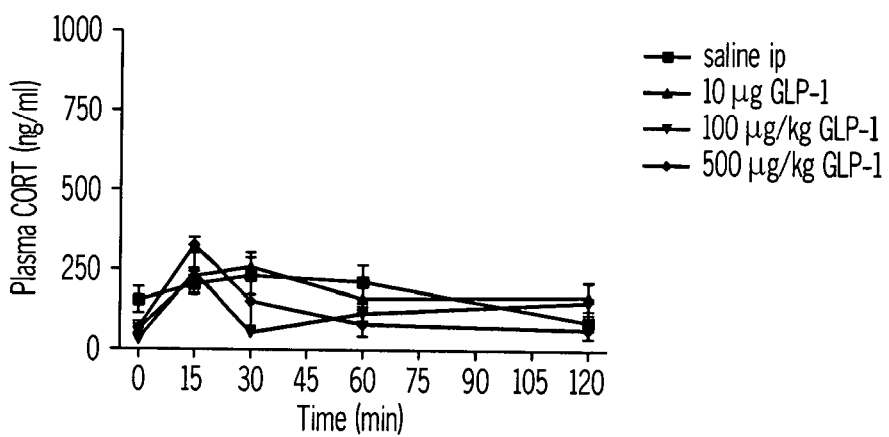
Figure 1D:
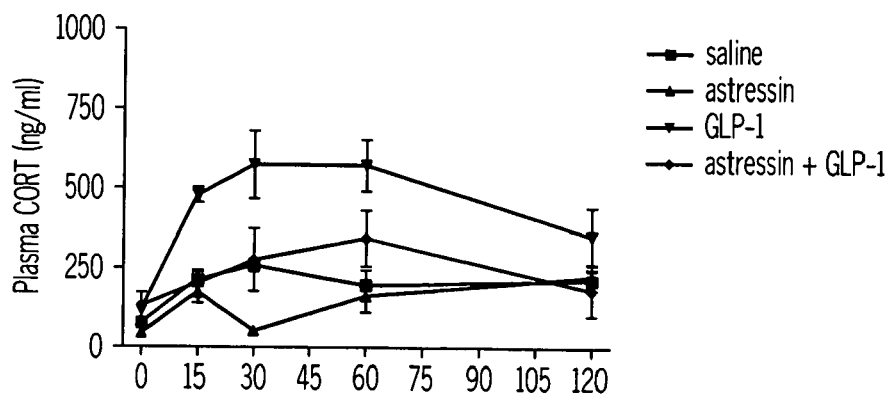
Figure 2:
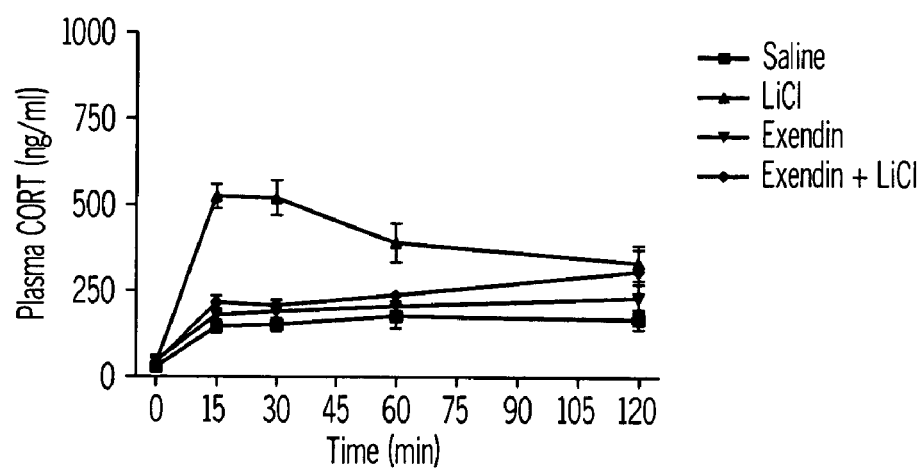

FIG. 2 presents plasma CORT levels at multiple time points following serial administration of saline and saline, saline and LiCl, exendin and saline, or exendin and LiCl. The first solution in each treatment was administered by intracerebroventricular injection; the second solution was administered by intraperitoneal injection. Plasma CORT levels at the time of treatment and at 15 minutes, 30 minutes, 60 minutes, and 120 minutes post-treatment are indicated in the graph. Plasma CORT levels are measured in ng/ml. Results obtained from saline administration are indicated with squares. Results obtained from administration of LiCl, exendin, and both LiCl and exendin are indicated with triangles, inverted triangles, and diamonds respectively.

Figure 3A:
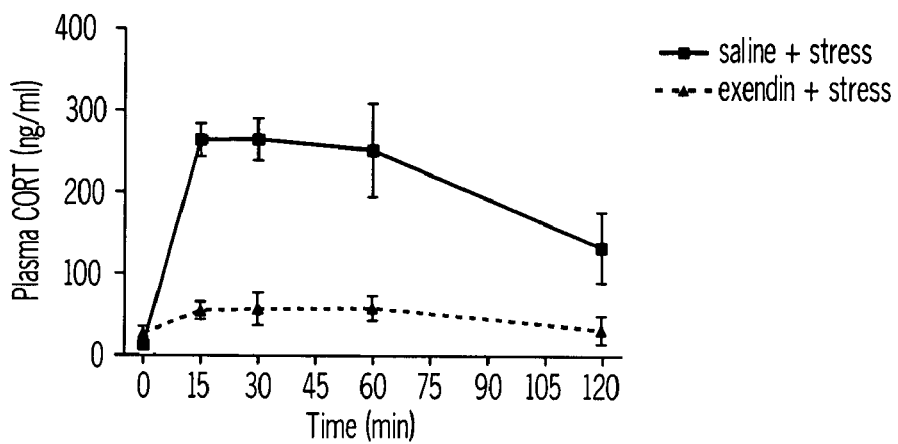
Figure 3B:
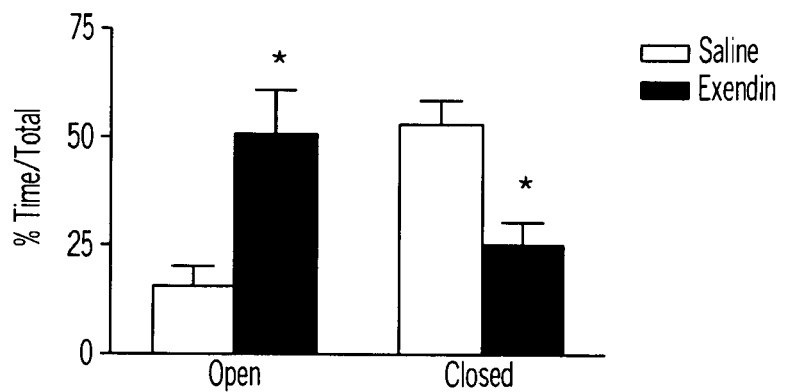

FIG. 3 presents results obtained from pretreated rats exposed to external stress. Rats were pretreated with either saline or exendin. Panel A presents plasma CORT levels obtained at 15, 30, 60, and 120 minutes after a 5 minute exposure to a modified elevated plus maze (EPM). Plasma CORT levels are measured in ng/ml. Results obtained from rats pretreated with saline are indicated with squares. Results obtained from rats pretreated with exendin are indicated with triangles. Panel B presents the percent time/total that saline-treated vs. exendin treated rats spent in the open as compared to the closed arms of an elevated plus maze.

Figure 4A:
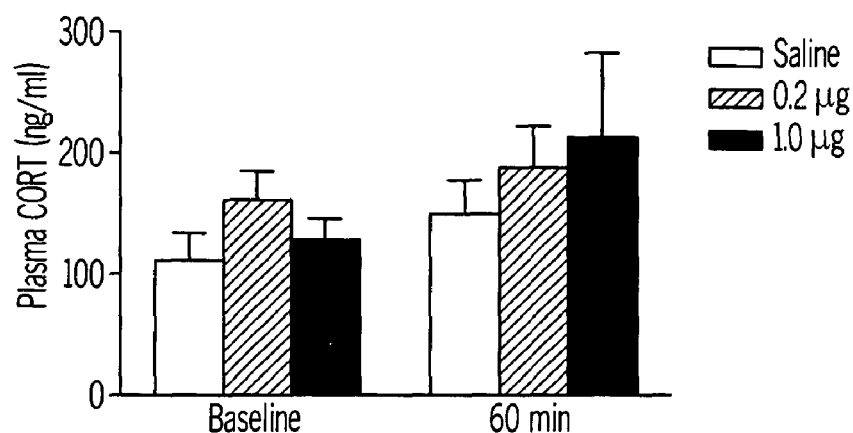
Figure 4B:
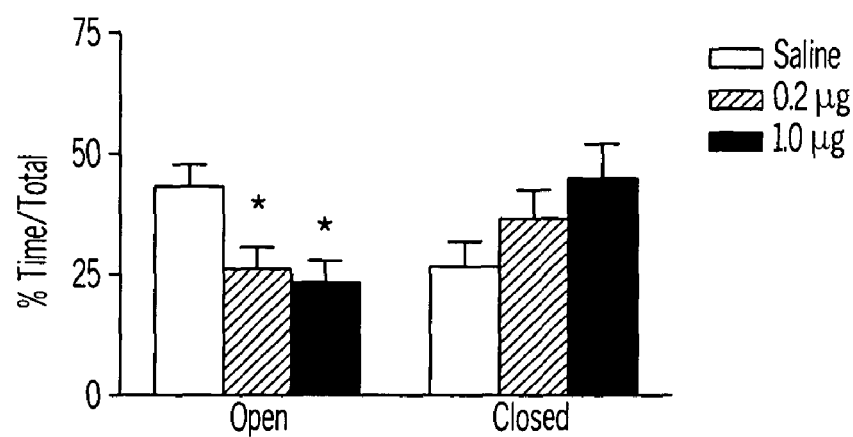

FIG. 4 presents results obtained from GLP-1 administration to the central nucleus of the amygdala (CeA) of rats. Results obtained from rats treated with saline are indicated with the white bar. Results obtained from rats treated with 0.2 μg GLP-1 or 1.0 μg GLP are indicated with the hatched bar or the solid bar respectively. Panel A presents plasma CORT levels at the time of treatment (baseline) and 60 minutes after treatment. Plasma CORT levels are measured in ng/ml. Panel B presents the percent time/total that saline-treated vs. GLP-1 treated rats spent in the open as compared to the closed arms of an elevated plus maze.

Figure 5A:
Figure 5B:
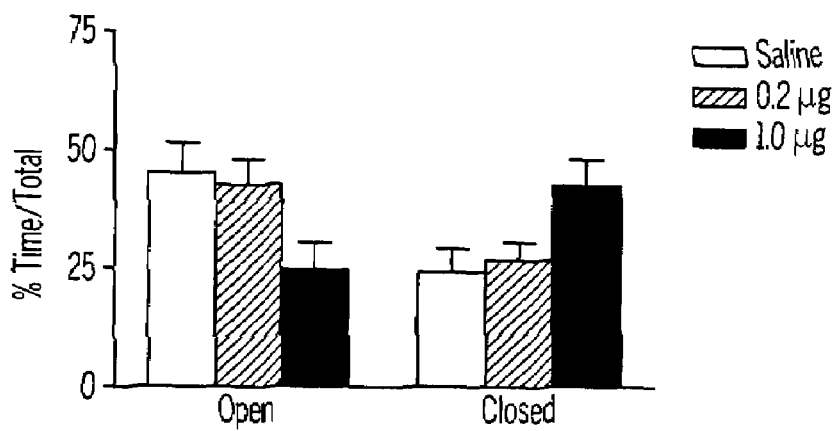

FIG. 5 presents results obtained from GLP-1 administration to the paraventricular nucleus of the hypothalamus (PVN). Results obtained from rats treated with saline are indicated with the white bar. Results obtained from rats treated with 0.2 μg GLP-1 or 1.0 μg GLP are indicated with the hatched bar or the solid bar respectively. Panel A presents plasma CORT levels at the time of treatment (baseline) and 60 minutes after treatment. Plasma CORT levels are measured in ng/ml. Panel B presents the percent time/total that saline-treated vs. GLP-1 treated rats spent in the open as compared to the closed arms of an elevated plus maze.

DETAILED DESCRIPTION

The invention is based, in part, on the novel observation that GLP-1 agonists or GLP-1 receptor (GLP1R) agonists arouse or activate the mammalian nervous system. Additionally, GLP-1 increases the stress response in vivo. In a related aspect, the invention concerns the discovery that GLP-1 antagonists, or GLP-1 receptor antagonists have sedative-like effects on the mammalian nervous system.

The identity of a novel role for the CNS GLP-1 system in regulating stress responses and anxiety has two important clinical implications. First, as GLP-1 agonists are developed for use as therapeutics to treat diabetes, great care should be taken to prevent their penetration into the CNS where they may inappropriately recruit these stress responses and contribute to stress-related diseases. Second, the broad role GLP-1 plays in mediating different aspects of the stress response implies that treatments that reduce GLP-1 signaling in the CNS may be viable options for the treatment of a variety of debilitating stress-related disorders or conditions ranging from panic attacks and anxiety to disorders associated with HPA dysregulation such as depression. Stress-related disorders include, but are not limited to, panic attacks, depression, drug abuse, post traumatic stress disorder, colitis, hypertension, asthma, Alzheimer's disease, schizoaffective disorders, sleep apnea, attention deficit syndromes with poor concentration, memory loss, forgetfulness, and narcolepsy, anxiety, movement disorder, aggression, psychosis, seizures, and sleep disorders.

The invention is based, in part, on the novel observation of the key role GLP-1 receptor (or GLP-1R) appears to play for two very disparate stressors. The data indicate a commonality of the neural circuits that mediate the response to both an interceptive and exteroceptive stressor.

The invention encompasses methods and compositions for altering the activity of the mammalian central nervous system. For example, by inactivating the GLP1R with receptor antagonist, or reducing activity of the GLP-1R receptor pathway (e.g., by binding a ligand to the receptor which impairs signal transduction) in neuronal cells, a sedative or anxiolytic effect on the central and/or peripheral nervous systems may be achieved. Alternatively, the state of arousal of the central nervous system in a subject may be increased by administering a GLP-1 agonist.

By "GLP-1 agonist" and "GLP-1 receptor agonist" is intended any agent, compound, peptide, or molecule that binds a GLP-1 receptor (GLP1R) in dispersed mammalian parietal cells and stimulates cAMP-dependent H+ production. See Schmidtler et al (1991) *Am. J. Physiol.* 260:G90, herein incorporated by reference in its entirety, for a more complete description of the assay. GLP-1 agonists include, but are not limited to, GLP-1, exendin 3, and exendin 4, (Raufman (1991) *Regulatory Peptides* 61:1-18, herein incorporated by reference in its entirety).

A number of other GLP-1R agonists are also known. Biologically active forms and derivatives of GLP-1 hormone which are useful in the methods of the invention are described in U.S. Pat. Nos. 5,120,712; 5,118,666; 5,512,549; 5,545,618; and 5,574,008, herein incorporated by reference in their entirety. Exendin 4(2-39) is also an agonist of the GLP-1R, as well as chimeras of GLP-1 and exendin 4, such as GLP-1(3-36)/extendin (31-39). See for example abstracts by Montrose-Rafizadeh et al. and Eng, J. in Diabetes, 45 (supplement 2): 152A. Similarly, exendin 3, also isolated from lizard venom, is yet another GLP-1R agonist.

By "GLP-1 antagonist" and "GLP-1 receptor antagonist" is intended any agent, compound, peptide, or molecule that binds a GLP-1 receptor in dispersed mammalian parietal cells and inhibits GLP-1-stimulated cAMP formation. A particularly potent antagonist of the GLP-1R receptor is exendin (9-39). Other modifications and/or peptide fragments of GLP-1 may be useful as antagonists, and may be identified by assays well known to those of skill in the art. For example, GLP-1(9-36) amide or GLP1(9-37) are known antagonists of the GLP-1R. Exendin 4(3-39) is yet another known antagonist of the GLP-1 receptor, as are exendin (4-39) through exendin (8-39). See for example Montrose-Rafizadeh et al., supra. Additionally, as noted above, certain antibodies to the extracellular domains of the GLP-1R may, instead of activating signal transduction through the receptor, antagonize signal transduction.

Any method which impairs activity of GLP-1R can be used to induce a sedative effect on the central and/or peripheral nervous system of a subject. Such approaches may be used to ameliorate nervous conditions requiring sedation or the alleviation of anxiety. These conditions include, but are not limited to, stress-related disorders, anxiety, movement disorder, aggression, psychosis, seizures, panic attacks, hysteria, and sleep disorders.

Any compound or peptide capable of binding to the GLP-1R is useful in the methods of the invention. For example, many transmembrane receptors are activated upon binding of an antibody fragment to the extracellular domain of the receptor. The methods of the invention encompass such antibodies to the GLP-1R extracellular domain, including humanized antibodies, antibody fragments such as Fab fragments, and single-chain antibodies. However, any antibodies to the extracellular domain should be characterized as either agonists or antagonists of the receptor using a cellular assay, e.g., the rat acinar cell assay of cAMP-dependent $H^+$ production.

Therapeutic treatment with a GLP-1 antagonist or GLP-1 receptor antagonist is administered so as to reduce or eliminate the symptoms in these patients associated with their nervous conditions. For example, a GLP-1 receptor antagonist is administered to a patient with a movement disorder such as dystonia in an amount sufficient to reduce the occurrence of aberrant and involuntary movements associated with the condition. Additionally, a GLP-1 antagonist or GLP-1 receptor antagonist may be administered to patients with a sleep disorder so as to induce sleep and thereby improve the mental status of such patients. Guidance for formulations, routes of administration, and dosages is provided below.

GLP-1R agonists activate the central nervous system in vivo. Methods of stimulating GLP-1 R receptor activity may be used to induce arousal for the treatment or amelioration of depression, schizoaffective disorders, sleep apnea, attention deficit syndromes with poor concentration, memory loss, forgetfulness, and narcolepsy, to name just a few. The therapeutic efficacy of the agonist treatment may be monitored by patient interview to assess their condition, by psychological/neurological testing, or by amelioration of the symptoms associated with these conditions. For example, treatment of narcolepsy may be assessed by monitoring the occurrence of narcoleptic attacks. As another example, effects of agonists of GLP-1 on the ability of a subject to concentrate, or on memory capacity, may be tested using any of a number of diagnostic tests well known to those of skill in art.

GLP-1 and GLP-1 receptor antagonists, including polypeptides, peptides, and fusion proteins, or compounds that are determined to antagonize GLP-1 activity such as exendin (9-39) or antibodies, can be administered to a patient at therapeutically effective amount to treat or ameliorate stress-related disorders. By "therapeutically effective amounts" is intended an amount sufficient to modulate the desired response. As defined herein, a therapeutically effective amount of GLP1-receptor antagonist (i.e., an effective dosage) ranges from about 0.001 to 30 mg/kg body weight, preferably about 0.01 to 3 mg/kg body weight, more preferably about 0.01 to 0.5 mg/kg body weight, and even more preferably about 0.01 to 0.3 mg/kg body weight.

Numerous factors may be taken into consideration by a clinician when determining an optimal dosage for a given subject. Primary among these is the amount of peptide hormone normally produced by the body. Circulating levels of GLP-1 in the body are normally in the range of 2 to 50 picoMoles per liter, depending upon the assay methodology used. Additional factors include the size of the patient, the age of the patient, the general condition of the patient, the particular disease being treated, the severity of the disease, the presence of other drugs in the patient, the in vivo activity of the peptide or peptide analog and the like. The trial dosages would be chosen after consideration of the results of animal studies and the clinical literature with respect to administration of peptide hormones and peptide hormone secretagogues. It will be appreciated by the person of ordinary skill in the art that information such as binding constants and $K_i$ derived from in vitro binding competition assays may also be used in calculating dosages.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of action, the nervous system, in order to minimize potential damage to other cells and tissues and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from animal studies. A dose may be formulated in animal models to achieve a circulating plasma concentration range that includes the $IC_{50}$ (i.e., the concentration of the test compound which achieves a half-maximal inhibition of symptoms). Such information can be used to more accurately determine useful doses in humans. Methods of measuring plasma levels of an agent are known in the art and include, but are not limited to high performance liquid chromatography and radioimmunoassay (as described elsewhere herein).

Central GLP-1 excites the HPA axis; peripheral GLP-1 does not. A novel observation is that GLP-1 acting in the CNS can elicit potent activation of the HPA axis at doses lower than that required to decrease food intake (Turton et al (1996) Nature 379:69-72; Tang-Christensen et al (1996) Am. J. Physiol. 271:R848-R856, van Dijk et al. (1997) Nature 385:214; herein incorporated by reference in their entirety). Guidance for determining dosages of GLP-1(7-36) amide appropriate for subcutaneous and intravenous administration in humans may be found in the following references: Ritzel et al., 1995, Diabetologia 38:720-725; Nauk et al., 1993, Diabetologia 36: 741-744; Willms et al., 1996, 81:327; Dupre et al., 1995, Diabetes 44:626; and Nauck et al., 1996, Diabetologia 39:1546-1553. Preferably, GLP-1 is administered to the subject in the range of 1 to 5 pM/kg body weight/minute intravenously, or 0.1 to 5 nM/kg body weight subcutaneously. Doses suitable for preferential modulation of the endocrine response to stress are preferably in the range of 0.001 to 30 mg/kg body weight, preferably about 0.01 to 3 mg/kg body weight, more preferably about 0.01 to 0.5 mg/kg body weight, and even more preferably about 0.01 to 0.3 mg/kg body weight Depending upon the specific activity of the GLP-1 agonist (or antagonist), the dosing regime may be adjusted up or down from that recommended for GLP-1(7-36) amide. For example, exendin 4 is at least 20 times more potent than GLP-1(7-36) amide in the mammalian central nervous system.

The mammalian stress response is multi-faceted and includes an endocrine response from the hypothalamic-pituitary-adrenal (HPA) axis and an anxiety response. In response to stress, stress-activated hormones are released by the HPA. Stress-activated hormones include, but are not limited to, adrenocorticotropin (ACTH) and glucocorticoids such as, but not limited to, corticosterone (CORT). The stress-activated hormones circulate in the plasma. Methods to assay hormone levels are known in the art and include, but are not limited to, chromatography and radioimmunoassay, as described elsewhere herein. Methods to assay effects of stress activated hormones are known in the art.

Formulations and Use.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration. Additionally, as described below by way of example, compounds for use in the present invention may be delivered directly to the brain.

For delivery directly to the central nervous system, delivery techniques should be preferably designed to cross the blood-brain barrier. For example, agonists and antagonists may be appended to agents which facilitate crossing of the blood-brain barrier (see PCT WO89/10134, which is incorporated by reference herein in its entirety). Alternatively, chemicals can be preadministered that make the blood brain barrier leaky to let peptides pass. Further, GLP-1 and GLP-1R agonists and antagonists may be directly delivered to the brain.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner. Examples of buccal formulations for GLP-1 are described in Gutniak et al., 1996, Diabetes Care 19:843. For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

EXPERIMENTAL

The following examples are offered by way of illustration and not limitation.

EXAMPLE 1

Effect of Central GLP-1 on the HPA Axis

Central GLP1 effects on the HPA axis were assayed as described in Kinzig et al. (2003) *J. Neuroscience* 21:6163-6170, herein incorporated by reference in its entirety). Ten male Long-Evans rats (275-350 gm) were housed individually in plastic tub cages with a 12 hour light/dark cycle. All rats were implanted with catheters in the inferior vena cava. Catheters were made of sterile SILASTIC tubing, the distal end beveled, a small piece sterile suture tied at 4 cm from the distal end, and filled with heparinized saline. The catheter was attached to a 1 ml syringe filled with heparinized saline at the end that remained at the head. Under ketamine (9 mg/kg, i.p.) and xylazine (1.5 mg/kg i.p.) anesthesia, the rat's abdomen and top of the head were shaved. A midline incision (approx. 8 cm in length) was made beginning at the sternum. An additional incision was made on the skull. The catheter was subcutaneously from the skull incision to the muscle wall lining the intraperitoneal cavity with a pair of straight hemostats. The muscle wall underlying the abdominal skin incision was opened. A small incision was made in the right muscle wall, through which the catheter was pulled into the intraperitoneal cavity. The inferior vena cava and surrounding area were cleared of fat by blunt dissection at the junction of the renal veins. Using blunt forceps, a tent was made of the inferior vena cava. The vein was then punctured with a 21 gauge needle, and the catheter was quickly inserted to the 4 cm mark. Heparinized saline (0.5 ml) was slowly pushed through the inserted catheter. One suture was made in the dorsal muscle wall immediately to the right of the insertion site. An additional suture was made to tie the catheter to the muscle wall 3 cm to the right of the insertion site. A small amount of the catheter was then pulled into the abdominal cavity, and the muscle wall and skin were sutured. The rats were then given 3 ml of warm water subcutaneously. After the inferior vena cava catheterization, rats were stereotaxically implanted with third ventricular cannulas. The catheter was cut at an appropriate length, attached to a blunted, bent 21 gauge needle and fixed to the skull with anchor screws and dental acrylic, as was the cannula. The end of the catheter elbow was covered with a small piece of polyethylene tubing with the end sealed.

Ten days after surgery, cannula placement was verified by administering angiotensin II through the cannula (intracerebroventricular, (i3vt)). Catheter patency was also determined 10 days after surgery. A 1 ml syringe was filled with saline and attached to 50 cm of PE 60 tubing. Saline was pushed through the tubing and the tubing was attached to the catheter elbow on the skull. Saline was pushed into the catheter, and blood was drawn to ensure patency. The blood was then pushed back into the catheter along with 0.6 ml of saline. Rats were handled daily for one week to acclimate them to the procedure (with the head cap and the catheter). On test day 1, a group of six rats received one of the following intracerebroventricular treatments: saline, 0.1 µg of GLP-1, 1.0 µg of GLP-1, or 10.0 µg GLP-1, all in a volume of 2 µl. Each rat was treated with each dose over a 3 week period, with no less than 5 days between each treatment. Testing began at 1 hour past the onset of the light cycle. At this time baseline blood was drawn into K+/EDTA vacutainer tubes. The rat was immediately injected with GLP-1 or saline. Fifteen, 30, 60, and 120 minutes after injection blood was drawn and placed on ice. After the last blood draw, the rats were given 1 ml of saline through the catheter. Blood was then centrifuged and plasma was removed and stored at −80° C. until processing.

Plasma was extracted and subsequently assayed (RIA) for ACTH and corticosterone (CORT). Results from one such experiment are presented in FIG. 1, panels A and B. Results were analyzed by two-way ANOVA and Tukey's HSD test.

EXAMPLE 2

Radioimmunoassay

Plasma ACTH and corticosterone concentrations were determined using $^{125}$I-labeled rat ACTH and corticosterone kits according to manufacturers' instructions. The limits of detection for each kit are 15 pg/ml and 8 ng/ml, respectively. For both ACTH and corticosterone assays, all plasma samples were run in duplicate in single assays.

EXAMPLE 3

Peripheral GLP1 Effects on the HPA Axis

An additional group of six rats was prepared as described in example 1 to test the effects of peripheral administration of GLP-1 on ACTH and corticosterone (CORT) release. Using a within-subjects design, rats were administered saline and 10, 100, and 500 µg/kg GLP-1 intraperitoneally. Each rat received each treatment in a randomized manner, with no less than 5 days between treatments. Results from one such experiment are presented in FIG. 1, panel C.

EXAMPLE 4

CRH Receptor Interaction Assay

Eight rats were implanted with inferior vena cava catheters and third ventricular cannulas as described in Example 1. Astressin is a nonselective CRH receptor antagonist. After recovery and acclamation time, the rats were subjected to the following treatments (n=6): intraperitoneal saline (1 ml)+i3vt saline (2 µl), intraperitoneal saline (1 ml)+i3vt GLP-1 (1.0 1 µg/2 µl); intraperitoneal astressin (33 µg/ml+i3vt saline (2 µl); and intraperitoneal astressin +i3vt GLP-1 1.0 µg/2 µl.

Blood was drawn from each animal at the start of the light phase. The rats were then immediately injected with the first of the paired injections. Fifteen minutes later, the second injection was made. Fifteen, 30, 60, and 120 minutes after the second injection, blood was drawn, transferred to a K$^+$-EDTA vacutainer, placed on ice. At the completion of the session, blood was processed as described elsewhere herein. Results from one such experiment are presented in FIG. 1, panel D.

EXAMPLE 5

GLP 1-R and Interceptive Stressor Interaction Assay

Twenty-four rats were implanted with inferior vena cava catheters and third ventricular cannulas as described in example 1. After recovery and acclamation time, the rats were weight-matched and divided into 4 groups (n=5 after testing of cannulas and catheters). Each group was subjected to one of the following treatments: i3vt saline (2 µl) plus intraperitoneal saline (0.15 M, volume equivalent to 2% of the animal's body weight), i3vt exendin (des-His$_1$, Glu$_9$-exendin-4; 50 µg/2 µl) plus intraperitoneal saline, i3vt saline (2 µl) plus intraperitoneal LiCl (0.15 M, volume equivalent to 2% of the animals body weight), and i3vt exendin plus intraperitoneal LiCl. Exendin is a GLP-1R antagonist. Injections were made, and blood samples were taken and processed as described in previous examples. Results are presented in FIG. 2.

EXAMPLE 6

Psychogenic Stressor Interaction with the HPA Axis

Twelve rats were implanted with inferior vena cava catheters and third ventricular cannulas. After recovery and acclamation time, the rats were weight-matched and divided into two groups (n=5 per group). On the test day, baseline blood was drawn from each rat. The rat was then immediately injected with saline or exendin. Group 1 received i3vt saline before placement on the elevated plus maze (EPM), and Group 2 received exendin (50 µg) before placement on the EPM. Fifteen minutes after injection, the rat was placed on the EPM for 5 minutes. Blood was drawn 15, 30, 60, and 120 minutes after EPM exposure and stored for processing as described in the previous experiments. Results from a typical experiment are presented in FIG. 3A.

EXAMPLE 7

Psychogenic Stress and Behavior Modification Assay

Twenty naïve rats were implanted with third ventricular cannulas as described. After verification of cannula placement, the rats were weight-matched and divided into two groups (n=8). On the test day, each rat was injected with saline or exendin 15 minutes before placement on the elevated plus maze. Group 1 received saline before EPM exposure, and group 2 received exendin (50 µg). After placement on the maze, each rat was videotaped for 5 minutes and later scored by an unbiased observer blinded to the experimental condition. The tapes were scored for the number of entries into the open arms versus the closed arms and for the amount of time spent in the open arms, closed arms, and the center of the maze. Results from a typical experiment are presented in FIG. 3B.

EXAMPLE 8

GLP-1 Agonist Effect on the Central Nucleus of the Amygdala

Twenty-five male Long-Evans rats (300-375 gm) were implanted with cannulas aimed at the central nucleus of the amygdala (CeA). After a two week recovery period, rats were weight-matched and divided into three groups (n=8 per group): saline, 0.2 µg GLP-1, or 1.0 µg GLP-1. All injections were delivered in a volume of 0.5 µl of 0.9% sterile saline via a Hamilton syringe over 2 minutes. Immediately before injection, blood samples were taken via tail vein. After injection, blood was again taken at 30 and 60 minutes. Blood was collected into heparinized Natelson tubes and then placed in 1.5 ml Eppendorf tubes on ice until the end of the experiment. Blood was then centrifuged and plasma extracted. The blood was processed as described in the previous experiments. Results from a typical experiment are presented in FIG. 4, panel A.

The rats were given a 5 day rest period and again weight matched and divided into 3 groups (n=8): saline, 0.2 µg GLP-1, or 1.0 µg GLP-1. Testing began at the onset of the dark cycle. Each rat was injected with GLP-1 or saline, with groups randomized such that the time of injection after the onset of the dark cycle was randomized. All injections were delivered in a volume of 0.5 µl of 0.9% sterile saline via a Hamilton syringe over two minutes. Fifteen minutes after injection the rat was placed on an elevated plus maze and videotaped for 5 minutes. Videotapes were later scored as described previously. Results from a typical experiment are presented in FIG. 4, panel B.

After completion of these studies, rats were given an overdose of sodium phenobarbital. Rats were then injected with 0.5 µl of cresyl violet via the cannula and decapitated. Brains were removed, passively perfused in 4% paraformaldehyde for 24 hours, and then sectioned at 50 µm thickness in the coronal plane. Sections were mounted on slides and examined for the presence of dye in the CeA, which indicated correct placement. Data from rats whose cannulas were not in the CeA were excluded from the analyses.

EXAMPLE 9

GLP-1 Agonist Effect on the Paraventricular Nucleus (PVN)

Twenty-two male Long-Evans rats (300-375 gm) were implanted with cannulas aimed at the hypothalamic PVN. After a two week recovery period, rats were weight-matched and divided into three groups (n=7): saline, 0.2 µg GLP-1, or 1 µg GLP1. All injections were delivered in a volume of 0.5 µl of 0.9% sterile saline via a Hamilton syringe over 2 minutes. Blood was taken from the tail vein and treated as described in Example 8. Results from a typical experiment are presented in FIG. 5, panel A.

The rats were given a 5 day rest period and again weight matched and divided into 3 groups (n=7): saline, 0.2 µg GLP-1, or 1.0 µg GLP-1. All injections were delivered in a volume of 0.5 µl of 0.9% sterile saline via a Hamilton syringe over 2 minutes. This experiment was conducted as described in Example 8. Results from a typical experiment are presented in FIG. 5, panel B.

After completion of these studies, rats were given an overdose of sodium phenobarbital. Rats were then injected with 0.5 µl of cresyl violet via the cannula and decapitated. Brains were removed, passively perfused in 4% paraformaldehyde for 24 hours, and then sectioned at 50 µm thickness in the coronal plane. Sections were mounted on slides and examined for the presence of dye in the PVN, which indicated correct placement. Data from rats whose cannulas were not in the PVN were excluded from the analyses.

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of sedating a mammalian subject, the method comprising the steps of:
   (a) providing a subject requiring sedation or the alleviation of anxiety; and
   (b) administering a peptide antagonist of the GLP-1 receptor to the mammalian subject in an amount sufficient to produce a sedative or anxiolytic effect on the mammalian subject, wherein said antagonist of the GLP-1 receptor is selected from the group consisting of exendin (9-39); GLP-1(9-36/37); exendin4(3-39); exendin (4-39) and exendin (8-39).

2. The method of claim 1, wherein the mammalian subject is a human being.

3. A method to modulate the effects of an elevated level of a stress-activated hormone within a mammalian subject, the method comprising the steps of:
   (a) providing a subject "having an elevated level of stress-activated hormone" requiring sedation or alleviation of anxiety; and
   (b) administering a peptide GLP-1 R antagonist to the mammalian subject, wherein the effects of said elevated level of a stress-activated hormone decrease, and wherein said GLP-1 R antagonist is selected from the group consisting of exendin (9-39); GLP-1(9-36/37); exendin4(3-39); exendin (4-39); and exendin (8-39).

4. A method to treat a stress-related disorder, said method comprising the steps of:
   (a) providing a mammalian subject exhibiting a stress-related disorder requiring sedation or the alleviation of anxiety; and
   (b) administering a therapeutically effective amount of a peptide GLP-1 receptor antagonist to said subject, wherein administering a therapeutically effective amount of a GLP-1 receptor antagonist produces a sedative or anxiolytic effect in said subject, and wherein said GLP-1 receptor antagonist is selected from the group consisting of exendin (9-39); GLP-1(9-36/37); exendin4(3-39); exendin (4-39) and exendin (8-39).

5. A method of sedating a mammalian subject, the method comprising the steps of:
   (a) providing a subject requiring sedation or the alleviation of anxiety; and
   (b) administering a peptide antagonist of the GLP-1 receptor to the mammalian subject in an amount sufficient to produce a sedative or anxiolytic effect on the mammalian subject, wherein said antagonist of the GLP-1 receptor is selected from the group consisting of exendin (9-39); GLP-1(9-36/37); exendin4(3-39); exendin (4-39); exendin (8-39).

6. The method of claim 5, wherein the antagonist of the GLP-1 receptor is administered intracerebroventricularly.

7. The method of claim 5, wherein the mammalian subject is a human being.

8. The method of claim 5, wherein the antagonist of the GLP-1 receptor is administered orally, subcutaneously, intramuscularly, or intravenously.

9. The method of claim 5, wherein the mammalian subject exhibits a stress-related disorder.

10. The method of claim 9, wherein said stress-related disorder is selected from the group consisting of: anxiety, aggression, psychosis, seizures, panic attacks, hysteria, and sleep disorders.

11. A method to modulate the effects of an elevated level of a stress-activated hormone within a mammalian subject, the method comprising the steps of:
    (a) providing a subject "having an elevated level of stress-activated hormone" requiring sedation or the alleviation of anxiety; and
    (b) administering a peptide (GLP-1 R antagonist to the mammalian subject, wherein the effects of said elevated level of a stress-activated hormone decrease, and wherein said GLP-1 R antagonist is selected from the group consisting of exendin (9-39);GLP-1 (9-36/37); exendin4(3-39); exendin (4-39); exendin (8-39); des- $His_1$, $Glu_9$ -exendin-4; exendin (5-39); exendin (6-39) and exendin (7-39).

12. The method of claim 11, wherein said stress-activated hormone is adrenocorticotropin.

13. The method of claim 11, wherein said stress-activated hormone is a glucocorticoid.

14. The method of claim 11, wherein said elevated stress-activated hormone results from internal stress.

15. The method of claim 11, wherein said elevated level of a stress-activated hormone results from external stress.

16. A method to treat a stress-related disorder, said method comprising the step of:
    (a) providing mammalian subject exhibiting a stress-related disorder requiring sedation or the alleviation of anxiety; and
    (b) administering a therapeutically effective amount of peptide GLP-1receptor antagonist to said subject, wherein administering a therapeutically effective amount of a GLP-1 receptor antagonist produces a sedative or anxiolytic effect in said subject, and wherein said GLP-1receptor antagonist is selected from the group consisting of exendin (9-39); GLP-1 (9-36/37); exendin4(3-39); exendin (4-39); exendin (8-39); des-$His_1$, $Glu_9$-exendin-4; exendin (5-39); exendin (6-39) and exendin (7-39).

17. The method of claim 16, wherein said GLP-1 receptor antagonist is administered intracerebroventricularly, orally, subcutaneously, intramuscularly, or intravenously.

18. The method of claim 16, wherein said therapeutically effective amount of a GLP-1 receptor antagonist is in the range of 0.001 to 30 mg/kg body weight.

19. The method of claim 16, wherein said therapeutically effective amount of a GLP-1 receptor antagonist is in the range of 0.01 to 3 mg/kg body weight.

20. The method of claim 16, wherein said therapeutically effective amount of a GLP-1 receptor antagonist is in the range of 0.01 to 0.5 mg kg body weight.

21. The method of claim 16, wherein said therapeutically effective amount of a GLP-1 receptor antagonist is in the range of 0.01 to 30 mg/kg body weight.

* * * * *